US005468619A

United States Patent [19]
Senyei et al.

[11] Patent Number: 5,468,619
[45] Date of Patent: Nov. 21, 1995

[54] SCREENING METHOD FOR IDENTIFYING WOMEN AT INCREASED RISK FOR IMMINENT DELIVERY

[75] Inventors: Andrew E. Senyei, San Juan Capistrano; David C. Casal, Mountain View, both of Calif.

[73] Assignee: Adeza Biomedical Corporation, Sunnyvale, Calif.

[21] Appl. No.: 61,755

[22] Filed: May 12, 1993

Related U.S. Application Data

[63] Continuation of Ser. No. 787,271, Nov. 4, 1991, abandoned.
[51] Int. Cl.$^6$ .................................................. G01N 33/543
[52] U.S. Cl. ............................ 435/7.94; 436/87; 436/510; 436/518; 436/814
[58] Field of Search .............................. 436/87, 548, 503, 436/510, 518, 65, 814; 435/7.92, 7.95, 7.94

[56] References Cited

U.S. PATENT DOCUMENTS 5,096,830  3/1992  Senyei et al. ............................ 436/65

FOREIGN PATENT DOCUMENTS

0316919A2  5/1989  European Pat. Off. ....... G01N 33/76

OTHER PUBLICATIONS

Leveno et al, *W. Obstetrics Suppl*, 12:1–11 (1987).
Oellerich, M., *J. Clin. Chem. Clin. Biochem.*, 22:895–904 (1984).
Wisdom, B. *Clin. Chem.*, 22:1243–1255 (1976).
Sekiguchi et al, *J. Biological Chem.*, 260:5105–5114 (1985).
Hayashi et al. *J. Biological Chem.*, 256:11292–11300 (1981).
Atherton et al, *Cell*, 25:133–141 (1981).
Kuusela et al, *Scand. J. Immunol.*, 12:331–337 (1980).
Matsuura et al, *Proc. Natl. Acad. Sci. USA*, 82:6517–6521 (1985).
Hess et al, *Obstet. Gynecol.* 68:25–28 (1986).
Ruoslahti et al, *Int. J. Cancer*, 27:763–767 (1981).
Lockwood et al,, "Increased plasma levels of EDI$^+$ cellular fibronectin precede the clinical signs of preeclampsia," *Am. J. Gynecol.* 162:358–362 (1990).
Lockwood et al–The New England J. of Med. vol. 325 No. 10 Sep. 5, 1991 pp. 669–674.
Atunkova et al–Chem Abst. vol. 115 (1991) pp. 205, 588b.
Bala et al, *Aust NZ Obstet. Gynecol*, 26:141–144 (1986).

*Primary Examiner*—Toni R. Scheiner
*Assistant Examiner*—James L. Grun
*Attorney, Agent, or Firm*—Skjerven, Morrill, MacPherson, Franklin & Friel; Laura Terlizzi; Emily M. Haliday

[57] ABSTRACT

The present invention provides an early, biochemical indication of increased risk of impending delivery. The method is particularly useful to identify those pregnant women who are at increased risk for preterm delivery and can also be used to identify those women at risk for a post-date delivery. The method comprises obtaining a cervicovaginal secretion sample from a pregnant patient after week 12 of gestation and determining the level of total fibronectin in the sample. The presence of an elevated fibronectin level in the sample indicates an increased risk of delivery. The test detects greater than 80% of women who deliver prematurely, as early as two to three weeks prior to delivery.

13 Claims, No Drawings

SCREENING METHOD FOR IDENTIFYING WOMEN AT INCREASED RISK FOR IMMINENT DELIVERY

This application is a continuation of application Ser. No. 07/787,271, filed Nov. 4, 1991, now abandoned.

BACKGROUND OF THE INVENTION

1. Field of the Invention

This invention relates to methods for detection of impending delivery, particularly impending preterm delivery. In particular, this invention is directed to the determination of impending delivery by detecting an increased level of total fibronectin in cervicovaginal secretion samples.

2. Description of the Prior Art

Determination of impending preterm births is critical for increasing neonatal survival of preterm infants. In particular, preterm neonates account for more than half, and maybe as much as three-quarters of the morbidity and mortality of newborns without congenital anomalies. Although tocolytic agents which can delay delivery were introduced 20 to 30 years ago, there has been only a minor decrease in the incidence of preterm delivery. It has been postulated that the failure to observe a larger reduction in the incidence of preterm births is due to errors in the diagnosis of preterm labor and to the patients' conditions being too advanced for tocolytic agents to successfully delay the birth.

Traditional methods of diagnosis of preterm labor have high false-negative and false-positive error rates [Friedman et al, *Am. J. Obstet. Gynecol.* 104:544 (1969)]. In addition, traditional methods for determining impending preterm delivery, particularly in patients with clinically intact membranes, may require subjective interpretation, may require sophisticated training or equipment [Garl et al, *Obstet. Gynecol.* 60:297 (1982)] or may be invasive [Atlay et al, *Am. J. Obstet. Gynecol.* 108:933 (1970)]. An early, objective biochemical marker which indicated increased risk for preterm delivery was sought.

Although preterm neonates account for the majority of the morbidity and mortality of newborns without congenital anomalies, post-date deliveries (deliveries after the due date of the baby) are also a significant source of morbidity and mortality. An early method of detecting impending delivery could also identify women late in gestation who are about to deliver and thus will not deliver post-date.

Recently, Lockwood et al [*New Engl. J. Med.*, 325:669–674 (1991)] reported that fetal fibronectin in cervical and vaginal secretions indicates pregnancies which are at risk of imminent delivery. The authors postulate that damage to the fetal membranes may release fetal fibronectin into the cervix and vagina, giving rise to the biochemical marker.

Other markers which may be released in women with true threatened pregnancies can be used to screen those women who should be closely monitored and to provide additional information about the stage of the disease.

SUMMARY OF THE INVENTION

The present invention provides an early, biochemical indication of increased risk of impending delivery. The method is particularly useful to identify those pregnant women who are at increased risk for preterm delivery. However, the method can also be used to detect those women who are at risk for post-date delivery. The method comprises obtaining a cervicovaginal secretion sample from a pregnant patient after about week 12 of gestation and determining the level of total fibronectin in the sample. The presence of an elevated fibronectin level in the sample indicates an increased risk of imminent delivery. The test is both a sensitive and specific screen for pregnancies at risk and can detect impending delivery about two to three weeks prior to delivery.

The test is preferably administered to women at about 12 weeks gestation and repeated at each perinatal visit (every two to four weeks) until at least week 37, preferably until delivery, if the test is negative. For those patients whose assay result indicates an increased risk of preterm delivery, a test of the patient's fetal fibronectin level can be made to confirm the increased risk and to estimate how soon the delivery may be. In addition, those patients can be carefully monitored, as are other patients at risk.

DETAILED DESCRIPTION OF THE INVENTION

The present invention is a screening assay which provides an early, biochemical indication of increased risk of imminent delivery. The method can provide an indication of impending delivery as early as two to three weeks prior to delivery. This method allows early intervention in the course of preterm delivery and provides an additional factor which can indicate those pregnancies at greatest risk. The method can also indicate those women late in gestation who are not likely to deliver in the next few weeks. Appropriate action to monitor or intervene in the impending post-date delivery can be taken.

The method comprises obtaining a cervicovaginal secretion sample from the vaginal cavity or the external cervical canal from a pregnant patient after about week 12 of pregnancy and determining the level of fibronectin in the sample. The presence of an elevated fibronectin level in the sample indicates a patient who is at risk for imminent delivery.

The present method can determine impending delivery from early in gestation through post-date deliveries. Deliveries prior to 20 weeks gestation are called spontaneous abortions rather than preterm deliveries. The present method can be used to detect spontaneous abortions (12 to 20 weeks gestation), preterm deliveries (20 to 37 weeks gestation), term deliveries (37 to 40 weeks gestation) and post-date deliveries (deliveries after 40 weeks gestation).

Patients to be Tested

The present method can be used on any pregnant woman following about 12 weeks gestation. In addition to screening any woman to determine whether delivery is imminent, the patients who should be screened are those patients with clinically intact membranes in a high risk category for preterm delivery, and preferably, all those women whose pregnancies are not sufficiently advanced to ensure delivery of a healthy fetus. Ninety percent of the fetal morbidity and 100 percent of the fetal mortality associated with preterm delivery is for those fetuses delivered prior to 32 to 34 weeks gestation. Therefore, 32 to 34 weeks gestation is an important cutoff for the health of the fetus, and women whose pregnancies are at least about 12 weeks and prior to 34 weeks in gestation should be tested.

In addition there are a large number of factors known to be associated with the risk of preterm delivery. Those factors include multiple fetus gestations; incomplete cervix; uterine anomalies; polyhydramnios; nulliparity; previous preterm rupture of membranes or preterm labor; preeclampsia; first trimester vaginal bleeding; little or no antenatal care; and symptoms such as abdominal pain, low backache, passage of cervical mucus and contractions. Any pregnant woman at 12 or more weeks gestation with clinically intact membranes and having one or more risk factors for preterm delivery should be tested throughout the risk period; i.e., until about week 37. Risk factors for spontaneous abortion include gross fetal anomalies, abnormal placental formation, uterine anomalies and maternal infectious disease, endocrine disorder cardiovascular renal hypertension, autoimmune and other immunologic disease, and malnutrition.

In addition, any woman who is late in gestation and may deliver post-date should be tested. Those patients include women after about week 37 through delivery. Risk factors for post-date deliveries include multiparity, maternal obesity, fetal macrosomia, advanced maternal age, previous post-date delivery, male fetus, and certain genetic disorders.

Sample

The sample is obtained in the vicinity of posterior fornix, the ectocervix or external cervical os. The sample generally comprises fluid and particulate solids, and may contain vaginal or cervical mucus and other vaginal or cervical secretions. The sample is preferably removed with a swab having a dacron or other fibrous tip. Alternatively, the sample can be obtained with a suction or lavage device. Calculations to account for any additional dilution of the samples collected using liquids can be performed as part of the interpretation of the assay procedure.

Following collection, the sample is transferred to a suitable container for storage and transport to a testing laboratory. It is important that the sample be dispersed in a liquid which preserves proteinaceous analytes. The storage and transfer medium should minimize, preferably prevent, decline in the analyte level during storage and transport. A suitable solution for storage and transfer consists of 0.05M Tris-HCl, pH 7.4; 0.15M NaCl, 0.02% NAN$_3$, 1% BSA, 500 Kallikrein Units/ml of aprotinin, 1 mM phenylmethylsulfonyl fluoride (PMSF) and 5 mM EDTA, and is described in U.S. Pat. No. 4,919,889, issued Apr. 24, 1990. The solution is also suitable as a sample diluent solution.

Alternatively, home and office use devices for immediate processing of the sample can be used. If used, the sample is placed directly in the device and testing is performed within minutes of sample collection. In such cases, the need to stabilize the analyte is minimized and any solution which facilitates performing the assay and is not detrimental to analyte stability can be used.

Assay Procedure

Fibronectin is assayed by any procedure which can determine the presence of a threshold quantity of fibronectin in the sample. Immunoassays are preferred. The antibody affinity required for detection of fibronectin using a particular immunoassay method will not differ from that required to detect other polypeptide analytes. The antibody composition can be polyclonal or monoclonal.

Anti-fibronectin antibodies can be produced by a number of methods. Polyclonal antibodies can be induced by administering an immunogenic composition comprising human fibronectin to a host animal. The fibronectin is preferably plasma fibronectin rather than cellular fibronectin or fetal fibronectin. Both the cellular and fetal isoforms contain extra domains (additional unique amino acid regions which are not present in plasma fibronectin). Thus, antibodies to those unique regions will not react with all fibronectin isoforms which may be present in the sample.

Preparation of immunogenic compositions of fibronectin may vary depending on the host animal and is well known. For example, fibronectin or an antigenic portion thereof can be conjugated to an immunogenic substance such as KLH or BSA or provided in an adjuvant or the like. The induced antibodies can be tested to determine whether the composition is fibronectin-specific. If a polyclonal antibody composition does not provide the desired specificity, the antibodies can be purified to enhance specificity by a variety of conventional methods. For example, the composition can be purified to reduce binding to other substances by contacting the composition with fibronectin affixed to a solid substrate. Those antibodies which bind to the substrate are retained. Purification techniques using antigens affixed to a variety of solid substrates such as affinity chromatography materials including Sephadex, Sepharose and the like are well known.

Monoclonal fibronectin-specific antibodies can also be prepared by conventional methods. A mouse can be injected with an immunogenic composition comprising fibronectin, and spleen cells obtained. Those spleen cells can be fused with a fusion partner to prepare hybridomas. Antibodies secreted by the hybridomas can be screened to select a hybridoma wherein the antibodies react with fibronectin and exhibit substantially no reaction with the other proteins which may be present in a sample. Hybridomas that produce antibodies of the desired specificity are cultured by standard techniques. Hybridoma preparation techniques and culture methods are well known and constitute no part of the present invention.

An exemplary preparation of polyclonal antibodies is described in the examples. Antibody preparation and purification methods are described in a number of publications including Tijssen, P. *Laboratory Techniques in Biochemistry and Molecular Biology: Practice and Theories of Enzyme Immunoassays* New York: Elsevier (1985), for example.

A number of different types of immunoassays are well known using a variety of protocols and labels. The assay conditions and reagents may be any of a variety found in the prior art. The assay may be heterogeneous or homogeneous, conveniently a sandwich assay.

The assay usually employs solid phase-affixed anti-fibronectin antibodies. The antibodies may be polyclonal or monoclonal. The solid phase-affixed antibodies are combined with the sample. Binding between the antibodies and sample can be determined in a number of ways. Complex formation can be determined by use of soluble antibodies specific for fibronectin. The antibodies can be labeled directly or can be detected using labeled second antibodies specific for the species of the soluble antibodies. Various labels include radionuclides, enzymes, fluorescers, colloidal metals or the like. Conveniently, the assay will be a quantitative enzyme-linked immunosorbent assay (ELISA) in which polyclonal antibodies specific for fibronectin are used as the solid phase-affixed and enzyme-labeled, soluble antibodies. Alternatively, the assay can be based on competitive inhibition, where fibronectin in the sample competes with a known amount of fibronectin for a predetermined amount of anti-fibronectin antibody. For example, any fibronectin present in the sample can compete with a known amount of the labeled fibronectin or fibronectin analogue for antibody binding sites. The amount of labeled fibronectin affixed to the solid phase or remaining in solution can be determined.

In another preferred embodiment, the assay is a homogeneous immunoassay in which polyclonal antibodies specific for fibronectin are used as the solid phase-affixed and colloidal metal-labeled, soluble antibodies. Appropriate dilution of the conjugate can be performed to detect the selected threshold level of fibronectin as a positive sample.

Threshold Value

The amount of total fibronectin in the sample is significantly elevated over the level for pregnant women at the same stage of gestation with normal pregnancies. Preferably, the total fibronectin concentration in the sample is at least about 600 to 750 ng/ml of sample after week 20 of gestation. Between weeks 12 and 20 the threshold values vary. Selected threshold values for the earliest portion of gestation are described in detail in the examples.

It is difficult to quantify proteins in vaginal swab samples for two reasons. The first is that the amount of fluid collected by the swab varies. The second is the total volume of secretions present in the cervicovaginal region varies. Therefore, any measurement of the fibronectin concentration in a particular sample is only a semi-quantitative indication of the total amount of fibronectin in the cervicovaginal region. Therefore, it is desirable that patients with samples near the threshold value be retested in a follow up visit.

A study determining that a threshold value after week 20 of gestation in the range of 600 to 750 ng/ml of sample is an indication of risk is described in detail in the examples.

Diagnostic screening methods to detect disease in the general population are conventionally designed to give very high sensitivity (detecting all those with disease) while sacrificing specificity (falsely detecting some who are free of disease). Because specificity is expected to be low in screening protocols, alternative (and usually more costly and sophisticated) diagnostic methods are typically used to confirm the existence of disease. Therefore, variations on the above threshold values can be made to make the assay either more specific or more sensitive.

Interpretation of Assay Result

Elevated levels of total fibronectin indicate increased risk of preterm delivery. As explained in detail in the examples, the assay is sensitive and specific. In addition, the assay has a high negative predictive value. That means that a large percentage of patients who delivered early had an elevated fibronectin value. Since the test successfully detects a large percentage of patients who deliver early, the test is an effective screening procedure for women at risk of a preterm delivery who do not have any other risk indicators.

The test can be administered to any pregnant woman following about 12 weeks gestation until delivery, or at least until the risk of premature delivery (i.e., until about week 37) ceases. Preferably, it is administered to all women with any known risk factor following 12 weeks gestation until delivery.

If the total fibronectin test is positive (above the threshold value), the patient is preferably tested for the presence of fetal fibronectin in her cervicovaginal secretions. If fetal fibronectin is present in the secretions, the patient is likely to deliver in two to three days. Measures to determine or enhance fetal lung maturity can be undertaken. If the fetal fibronectin assay is negative, the patient should be carefully monitored and repeated evaluations of the patient's fetal fibronectin levels should be performed on subsequent visits. In general, patients at risk for preterm delivery are examined every two weeks from about 22 to 36 weeks, rather than every four weeks as for patients in a low risk category. All patients are examined weekly from about week 36.

If the total fibronectin test is negative, the test is preferably repeated on each subsequent antenatal visit until either the test is positive or the patient has delivered her baby.

This invention is further illustrated by the following specific but non-limiting examples. Temperatures are given in degrees Centigrade and concentrations as weight percent unless otherwise specified. Procedures which are constructively reduced to practice are described in the present tense, and procedures which have been carried out in the laboratory are set forth in the past tense.

EXAMPLE 1

Quantitation of Total Fibronectin in a Vaginal Swab Sample

An immunoassay to determine total fibronectin in a vaginal sample used the reagents and procedures described below.

Preparation of Polyclonal Anti-Human Fibronectin Antibody

Human plasma fibronectin was purified from human plasma as described by Engvall and Ruoslahti, *Int. J. Cancer* 20:1–5 (1977). The anti-human plasma fibronectin antibodies were elicited in goats using the immunization techniques and schedules described in the literature, e.g., Stollar, *Meth. Enzym.* 70:70 (1980), immunizing the goats with the human plasma fibronectin antigen. The antiserum was screened in a solid phase assay similar to that used for monoclonal antibodies, e.g., as described by Lange et al, *Clin. Exp. Immunol.* 25:191 (1976) and Pisetsky et al, *J. Immun. Meth.* 41:187 (1981).

The IgG fraction of the antiserum was purified further by affinity chromatography using CNBr-Sepharose 4B (Pharmacia Fine Chemicals) to which has been coupled human plasma fibronectin according to the method recommended by the manufacturer (AFFINITY CHROMATOGRAPHY, Pharmacia Fine Chemicals Catalogue 1990), pp 15–18.

Briefly, the column was equilibrated with from 2 to 3 volumes of buffer (0.01 M PBS, pH 7.2), and the anti-human fibronectin antibody-containing solution was then applied to the column. The absorbency of the effluent was monitored at 280 nm until protein no longer passed from the column. The column was then washed with equilibration buffer until a baseline absorbance at 280 nm was obtained.

The immunoaffinity bound anti-human plasma fibronectin antibody was eluted with 0.1M glycine buffer, pH 2.5. Peak protein fractions were collected, pooled and dialyzed against 0.01M PBS, pH 7.2, for 24–36 hr at 4° C. with multiple buffer changes.

The above procedure was repeated to immunize rabbits with human plasma fibronectin and to purify the resultant polyclonal anti-human fibronectin antibodies.

Preparation of Anti-Fibronectin Antibody-Coated Microtiter Plate

Goat anti-human plasma fibronectin prepared as described above was diluted to 10 μg/ml in 0.05M carbonate buffer, pH 9.6. 100 μl was dispersed into each well of a polystyrene microtiter plate such as supplied by Costar, Nunc, or Dynatech. The plate was covered and incubated 2 to 4 hr at room temperature or 4° C. overnight. The plate was washed 3 to 4 times with Wash Buffer (0.02M Tris HCl, 0.015M NaCl, 0.05% TWEEN-20), filling and emptying the wells completely with each use. The plate was then blocked by dispersing 200 μl of a blocking/stabilizing solution (4% sucrose, 1% mannitol, 0.01M PBS, 1% BSA, 0.02% $NAN_3$, pH 7.4) into each well and incubating for 30 minutes to 2 hrs at room temperature. The wells were then aspirated to dryness, the plate was packaged in an air-tight container with a desiccant pouch, and stored at 4° C. until needed. The wells were present as eight well strips.

Preparation of Enzyme Labeled Anti-(fibronectin) Antibody

Anti-human plasma fibronectin antibody prepared as described above was conjugated with alkaline phosphatase following the one-step glutaraldehyde procedure of Avrameas, *Immunochem.* 6:43 (1969).

Assay Reagents

The assay was performed using the following additional reagents. The stock antibody conjugate was appropriately diluted in conjugate diluent (0.05M Tris Buffer pH 7.2, 2% D-Sorbitol, 2% BSA, 0.1% Sodium Azide, 0.01% Tween-20, 1 mM Magnesium Chloride, and 0.1% Zinc Chloride) and 10 ml placed in a polyethylene dropper bottle container.

The enzyme substrate (10 ml in a polyethylene dropper bottle container) was phenolphthalein monophosphate (1 mg/ml) dissolved in 0.4M aminomethylpropanediol buffer, pH 10 with 0.1 mM magnesium chloride and 0.2% sodium azide.

The fibronectin calibration solutions were plasma fibronectin (fibronectin from human serum purchased from Boehringer Mannheim, Indianapolis, Ind.; Catalogue No. 1050407) diluted to a concentration of 0.0, 0.01, 0.05 and 0.25 μg/ml in sample diluent solution (0.05M Tris buffer pH 7.4, 1% bovine serum albumin (BSA), 0.15M sodium chloride, 0.02% Sodium Azide, 5 mM ethylenediamine tetraacetic acid (EDTA), 1 mM phenylmethylsulfonyl fluoride (PMSF), and 500 Kallikrein Units/ml of Aprotinin). This sample diluent solution is described in U.S. Pat. No. 4,919,889 to Jones et al, issued Apr. 24, 1990, which patent is incorporated herein by reference in its entirety. The negative control was the sample diluent solution used for the positive control without fibronectin.

The rinse buffer (10 ml in a polyethylene dropper bottle container) was a 50X concentrate containing 1.0M Tris buffer pH 7.4, 4.0M sodium chloride, 2.5% Tween-20, and 1% sodium azide. The rinse buffer was diluted with water to a final concentration of 0.02M Tris, 0.08M sodium chloride, 0.05% Tween-20, and 0.02% sodium azide for use in the assay.

In addition, 5μ pore size polyethylene sample filters (Porex Technologies, Fairburn, Ga.) were used to filter the samples prior to assay. All of the dropper bottles used to perform the assay were polyethylene bottles designed to dispense approximately 50 μl drops of the reagent. All of the assay steps performed following sample collection utilized the reagents and materials described above.

Assay Procedure

The assay was performed as follows. All samples were collected in the vicinity of the posterior fornix or cervical os using dacron swabs. Swab samples were immersed in 1.0 ml of sample diluent in a collection vial. The swabs were removed from the solution leaving as such liquid as possible in the collection tube. The samples were incubated at 37° C. along with the controls for 15 minutes prior to the assay, either before or after filtration. A sample filter was snapped in place on each sample tube. The 8-well strips were snapped into place in a strip holder. The holder had the alphanumeric indications of the 12 columns and eight rows of standard microtiter plates. Duplicate 100 μl aliquots of each sample and the positive and negative controls were placed in separate wells of the microtiter strip and incubated for 1 hour at room temperature.

Following incubation, samples and controls were aspirated from the wells. Wells were washed three times with diluted wash buffer (1X). Following washing, 100 μl of enzyme-antibody conjugate was added to each well and incubated for 30 minutes at room temperature. The wells were aspirated and washed as described above. Following washing, 100 μl of enzyme substrate was added to each well and incubated for 30 minutes at room temperature.

Following the incubation, the plates were gently agitated by hand or with an orbital shaker to mix the well contents. The frame of strips was placed in an ELISA plate reader. The absorbance of each well at 550 nm was determined. The average absorbance of the duplicate wells for each sample and control was calculated. The total fibronectin concentration for the samples was calculated by preparing a standard curve and estimating that the samples were diluted to about one-tenth of their original concentration (collection of about 0.1 ml of sample combined with 1.0 ml of diluent).

EXAMPLE 2

Detection of a Threshold Amount of Total Fibronectin in a Vaginal Swab Sample

In another preferred embodiment, an assay kit to detect a threshold amount of fibronectin includes the following components. This kit is designed to be used to perform a rapid, bedside or doctor's office assay.

1. an assay device comprising a plastic housing and containing:
   (a) a porous nylon membrane to which is bound an anti-fibronectin antibody;
   (b) a flow control membrane system; and
   (c) an absorbent layer
2. a colloidal gold-labeled goat anti-fibronectin antibody conjugate in a protein matrix
3. conjugate reconstitution buffer
4. a wash solution
5. a sterile, dacron sample collection swab The membrane device is prepared by the following procedure. Approximately 2 μl of the polyclonal anti-fibronectin antibody prepared as described in Example 1 is applied to a membrane surface (1.2μ nylon, Biodyne-A, Pall) in a pH 6, 0.01M phosphate buffered saline (PBS), 0.1 M citrate buffer containing 0.5 mg/ml BSA. A procedural control consisting of human plasma fibronectin purified as described in Example 1 in the same buffer is also applied to a discrete region of the membrane. After the membrane has air dried, a blocking reagent of PBS-buffered, 0.5% nonfat dry milk is added to the membrane. The excess blocking reagent is removed after at least about 20 minutes.

The membrane-holding device (Target Device, V-Tech, Pomona, Calif.) is assembled with a second porous layer (0.45μ low protein-binding nylon, LoProdyne, Pall) beneath the antibody-bearing membrane (in the direction of sample application) for controlling the flow of sample solution from the assay membrane to the absorbent layer. The two porous membranes are then placed over an absorbent porous polyethylene layer having a capacity of greater than 1.5 ml (Chromex, Brooklyn, N.Y.) and enclosed in the device. The device is packaged individually in a sealed plastic bag containing desiccant.

The colloidal gold was prepared by the reduction of 0.01% tetrachloroauric acid with 0.16% sodium citrate in a manner which produces approximately 30 nm particles. Briefly, the two solutions are heated separately to 90° C. The reducing solution is added to the gold solution while vigorously stirring. The combined solution is boiled (100° C.) for at least 10 minutes.

Affinity purified goat anti-fibronectin antibody (prepared as described in Example 1) was bound to the colloidal gold by adsorption. Briefly, the colloidal gold solution prepared above was combined with the antibody (5–10 µg/ml) in water. Following conjugation, the conjugate solution is stabilized by the addition of 5% BSA and 5% polyvinylpyrrolidone (final concentration).

The stock conjugate was concentrated approximately 10- to 12-fold by ultrafiltration using a hollow fiber filter. The concentrated conjugate was diluted to an appropriate level in 15 mM Tris, 2% BSA, 0.1% Tween 20, 0.2% polyethylene glycol, 8% polyvinylpyrrolidone and 0.04% thimerosal. An appropriate concentration is determined by using a range of dilutions in a sample assay procedure as described below and determining the dilution which produces the best result. This titration procedure is used to set the threshold detection level for total fibronectin at 750 ng/ml.

The selected conjugate dilution is placed in polyethylene sample collection tubes and lyophilized. The tubes are fitted with 2µ pore size polyethylene sample filters (Porex Technologies, Fairburn, Ga.) during the lyophilization process. The lyophilized conjugate is individually packaged in a foil pouch with desiccant.

The conjugate reconstitution buffer is 100 mM sodium acetate. This buffer is packaged as a unit dose in a 1 ml disposable tube. The wash solution is water packaged as a unit dose in a disposable tube. The kit additionally contains an individually packaged sterile dacron swab and a procedural summary card.

The assay was performed as follows.

1. Before collecting the sample, remove the plastic tube containing gold conjugate from the foil pouch, remove the dropper tip and add the entire contents of the tube containing the conjugate reconstitution buffer.
2. Collect the sample with the swab provided. During a sterile speculum examination, insert the swab into the posterior fornix of the vagina, twirl for approximately 10 seconds to absorb fluid. Immediately proceed to perform the test. Samples may not be stored for later testing. Place the swab in the gold conjugate solution and mix rapidly with an up and down motion for 10 to 15 seconds.
3. Remove as much liquid as possible from the swab by rolling the tip on the inside of the tube. Dispose of the swab in a manner consistent with handling potentially infectious materials.
4. Replace the dropper tip on the plastic tube and immediately dispense the entire volume of diluted filtered sample onto the surface of the membrane device.
5. After the sample liquid has been absorbed into the membrane surface, add a few drops of wash solution and observe the results.
6. A negative result is indicated by a red color in the procedural control area of the membrane only. A positive result is indicated by a pink or red spot in the test zone of the membrane as well as in the control zone.

EXAMPLE 3

Total Fibronectin Levels in Preterm Patients

In an effort to evaluate cervicovaginal expression of total fibronectin as a screen for preterm delivery (preterm delivery), 73 asymptomatic women with elevated risk for preterm delivery were identified and followed longitudinally. Factors which defined these women as having higher risk included pregnancy with twins, uterine anomalies, previous preterm labor and previous preterm delivery. Vaginal specimens were obtained from these women at 1 to 2 week intervals between 24 and 34 weeks gestation. Vaginal secretions were collected from the ectocervical region of the external cervical os and the posterior fornix of the vagina using separate dacron swabs.

The total fibronectin concentration of vaginal secretion samples in this study was determined as described in Example 1. The average concentration of total fibronectin in cervicovaginal secretions was 4.49±0.50 µg/ml (mean±SEM) for women with uncomplicated pregnancies prior to 22 weeks gestation. The concentration of total fibronectin exceeded 750 ng/ml in 64.8% (250/386) of these women. After 22 weeks gestation the average concentration of total fibronectin was 0.99±0.50 and 22.2% (4/18) had values greater than 750 ng/ml.

From those values, a sample was determined to be positive if its total fibronectin concentration exceeded 750 ng/ml. A single positive sample was the minimal requirement for definition of a positive patient. The sample results for all women were accumulated and compared to gestational age at the time of delivery. Delivery prior to 37 weeks and 0 days was defined as preterm while a pregnancy exceeding 37 days and 0 days was defined as term.

Of the 73 patients enrolled in this evaluation, 24 delivered prematurely and 49 delivered at term. The relationship of total fibronectin results and clinical outcome is shown in Table 1. In the analyses, sensitivity means the number of true positive test results divided by the total number of women with the condition; i.e., the number of true positive test results divided by the sum of the number of true positive and false negative test results). Specificity means the number of true negative test results divided by the total number of women without the condition; i.e., the number of true negative test results divided by the sum of the number of true negative and false positive test results. Positive predictive value (PV+) means the number of true positive test results divided by the total number of samples which tested positive. Negative predictive value (PV−) means the number of true negative test results divided by the total number of samples which tested negative. Sensitivity, specificity, positive predictive value and negative predictive value are based on detection of preterm delivery (PTD), rather than term delivery (TD) in this analysis.

|  | FN + | FN − |  |
| --- | --- | --- | --- |
| PTD | 19 | 5 | 24 |
| TD | 24 | 25 | 49 |

-continued

|  | FN + | FN − |  |
|---|---|---|---|
|  | 43 | 30 | 73 |

Sensitivity = 82.8%
Specificity = 51.0%
PV + = 44.2%
PV − = 83.3%
Relative Risk = 2.65, p < 0.007
Mantel-Haenszel $X_2$ = 5.98, p < 0.014

At least one total fibronectin sample exceeded 750 ng/ml in 19 of 24 patients (sensitivity=82.8%) delivering prematurely and 24 of 49 patients delivering at term (specificity= 51.0%). Alternatively, the predictive value of a positive test was 44.2% while the predictive value of a negative test was 83.3%. The relative risk associated with a positive test (relative to a negative test) was 2.65 which is significantly different from 1.00 (Null Hypothesis ($H_o$: Relative Risk= 1.00) with a p value of less than 0.007. Moreover, the distribution of positive results was associated with preterm delivery as shown by the Mantel-Haenszel $X_2$ test statistic of 5.98 (p<0.014).

The results of the study demonstrate that the test was sensitive and acceptably specific for screening in that most women who deliver early are detected by the test.

EXAMPLE 4

Total Fibronectin Levels in Weeks 12 to 22

Total fibronectin concentrations were determined in specimens of cervicovaginal secretions obtained from women with apparently uncomplicated pregnancies between 12 weeks gestation and term as described in Example 1. Average concentrations of total fibronectin were determined at each gestational age.

Total fibronectin concentration was highest at 12 weeks gestation and gradually decreased until week 22. From week 22 of gestation until near term, total fibronectin concentration rarely exceeded 500 ng/ml. As gestational age advanced beyond 34 weeks, total fibronectin concentrations gradually increased presaging delivery. The gestational age dependency of total fibronectin concentration was accurately predicted by a series of second order polynomial regression equations calculated using estimated gestational age at sampling and total fibronectin concentration as the independent and dependent variables, respectively.

The predicted concentrations of total fibronectin (μg/ml) at each week of gestation are shown in the following table.

| Gestational Age | Pred [Total FN] | Gestational Age | Pred [Total FN] |
|---|---|---|---|
| 12 | 6.30 | 25 | 0.10 |
| 13 | 6.20 | 26 | 0.06 |
| 14 | 5.94 | 27 | 0.03 |
| 15 | 5.51 | 28 | 0.04 |
| 16 | 4.92 | 29 | 0.07 |
| 17 | 4.16 | 30 | 0.13 |
| 18 | 3.24 | 31 | 0.22 |
| 19 | 2.16 | 32 | 0.33 |
| 20 | 0.91 | 33 | 0.47 |
| 21 | 0.57 | 34 | 0.64 |
| 22 | 0.42 | 35 | 0.83 |
| 23 | 0.29 | 36 | 1.06 |
| 24 | 0.18 | 37 | 1.31 |
|  |  | 38 | 1.58 |

What is claimed is:

1. An immunoassay method of screening for an increased risk of impending delivery comprising:
    a) obtaining a secretion sample from the vaginal cavity or the cervical canal from a pregnant patient after week 12 of pregnancy; and
    b) determining the level of total fibronectin in the sample, wherein an elevated
    level of total fibronectin in the sample suggests an increased risk of impending delivery.

2. The method of claim 1 wherein the sample is obtained from the posterior fornix.

3. The method of claim 1 wherein the sample is obtained from the cervical os.

4. The method of claim 1 wherein the sample obtained from the patient is determined not to have an elevated total fibronectin level and the method further comprises repeating the steps of the method with at least one other sample from the patient obtained at least two weeks after the sample determined not to have an elevated total fibronectin level was obtained.

5. The method of claim 4 wherein said other sample is obtained 2 weeks to about 4 weeks after obtaining the sample and the steps of the method are repeated with a succession of one or more other samples until the patient delivers or a sample determined to have an elevated total fibronectin level is obtained.

6. The method of claim 1 wherein the sample is determined to have an elevated total fibronectin level and the method further comprises performing a second immunoassay to determine the presence of fetal fibronectin in a sample of cervicovaginal secretions obtained from the patient wherein determination of the presence of fetal fibronectin by said second immunoassay confirms the increased risk of impending delivery.

7. The method of claim 6 wherein the sample of cervicovaginal secretions is determined not to contain fetal fibronectin and the method further comprises repeating the determination of fetal fibronectin with at least one other sample of cervicovaginal secretions from the patient obtained at least one week after the sample determined not to contain fetal fibronectin was obtained.

8. The method of claim 7 wherein said other sample of cervicovaginal secretions is obtained 2 weeks after obtaining the sample and the determination of fetal fibronectin is repeated with a succession of one or more other samples obtained at two week intervals until the patient delivers or a sample positive for fetal fibronectin is obtained.

9. The method of claim 1 wherein the determining step comprises the steps of:
    a) contacting the sample with a first anti-(total fibronectin) antibody for a time sufficient for antigen-antibody binding; and
    b) determining the amount of binding to determine the level of total fibronectin in the sample.

10. The method of claim 9 wherein said first anti-(total fibronectin) antibody is affixed to a solid phase and the amount of binding is determined by:
    a) contacting the sample with a second anti-(total fibronectin) antibody for a time sufficient for antigen-antibody binding, said second anti-(total fibronectin) antibody being directly or indirectly labeled; and b) determining the amount of label on said second antibody specifically bound to the solid phase to determine the level of total fibronectin in the sample.

11. The method of claim 10 wherein the labeled anti-(total fibronectin) antibody is conjugated to a label.

12. The method of claim 11 wherein the label is an enzyme.

13. The method of claim 10 wherein the labeled anti-(total fibronectin) antibody is indirectly labeled by reacting the anti-(total fibronectin) antibody with a labeled antibody specific for the anti-(total fibronectin) antibody.

* * * * *

UNITED STATES PATENT AND TRADEMARK OFFICE
CERTIFICATE OF CORRECTION

PATENT NO.    :   5,468,619
DATED         :   November 21, 1995
INVENTORS     :   Andrew E. Senyei and David C. Casal It is certified that error appears in the above-identified patent and that said Letters Patent is hereby corrected as shown below:

At column 3, line 40 and column 7, line 6:
  Delete "NAN$_3$" and substitute therefor --NaN$_3$--.

At column 8, line 2:
  Delete "such" and substitute therefor --much--.

Signed and Sealed this

Eleventh Day of February, 1997

Attest:

Attesting Officer

BRUCE LEHMAN

Commissioner of Patents and Trademarks